United States Patent [19]

Tanaka et al.

[11] Patent Number: 5,210,246

[45] Date of Patent: May 11, 1993

[54] AMINO GROUP-CONTAINING SILICATE COMPOSITION AND DEHYDRATING AGENT CONTAINING IT

[75] Inventors: Tetsuya Tanaka, Fujisawa; Hiroaki Katano; Masaaki Ohtani, both of Yokohama, all of Japan

[73] Assignees: Mitsubishi Kasei Corporation; Dow Mitsubhishi Kasei Limited, both of Tokyo, Japan

[21] Appl. No.: 688,558

[22] PCT Filed: Oct. 19, 1990

[86] PCT No.: PCT/JP90/01347

§ 371 Date: Jun. 20, 1991

§ 102(e) Date: Jun. 20, 1991

[87] PCT Pub. No.: WO91/05790

PCT Pub. Date: May 2, 1991

[30] Foreign Application Priority Data

Oct. 20, 1989 [JP] Japan .................. 1-273021

[51] Int. Cl.⁵ ................. C07F 7/10; C08G 77/02
[52] U.S. Cl. ..................... 556/413; 525/123; 528/45
[58] Field of Search ............ 556/413; 525/123, 127; 528/45

[56] References Cited

U.S. PATENT DOCUMENTS 3,079,656  3/1983  Emblem et al. .......... 22/193
4,722,969  2/1988  Huynh-Tran et al. .......... 525/123

FOREIGN PATENT DOCUMENTS 1547331  11/1968  France .
45-26233  8/1970  Japan .
46-30711  9/1971  Japan .
1-156368  6/1989  Japan .
1519657  8/1978  United Kingdom .

OTHER PUBLICATIONS

Chemical Abstracts, vol. 76, No. 16, Apr. 17, 1972, p. 38, Abstract No. 86647v & SU-A-292 489.

Primary Examiner—Arthur C. Prescott
Attorney, Agent, or Firm—Oblon, Spivak, McClelland, Maier & Neustadt

[57] ABSTRACT

The present invention relates to a reaction product of a tetraalkoxysilane or a silicate oligomer obtained by its partial hydrolysis-dehydration-polycondensation, with an amino alcohol having one or two hydroxyl groups, and a dehydrating agent comprising such a reaction product.

The dehydrating agent of the present invention is suitable for dehydrating a moisture at a level of a few hundreds ppm. Further, since an amino alcohol is formed by the dehydration, it is particularly useful as a dehydrating agent for a raw material for the production of a urethane resin or an epoxy resin.

16 Claims, 1 Drawing Sheet

AMINO GROUP-CONTAINING SILICATE COMPOSITION AND DEHYDRATING AGENT CONTAINING IT

TECHNICAL FIELD

The present invention relates to an amino group-containing silicate composition suitable for dehydrating a very small amount of moisture contained in various chemical reagents. Further, the present invention relates to a dehydrating agent employing such a composition and a resin produced by using a raw material dehydrated by means of such a composition.

BACKGROUND TECHNIQUE

Many chemical reagents and chemical raw materials have their moisture contents stipulated in the product standards. It is evident from this fact that it is very important to control or dehydrate the moisture in chemical reagents and chemical raw materials.

As a dehydration method, it has been common to separate the moisture and the product by distillation or fractional distillation. However, in many cases, it is difficult to completely remove the moisture by distillation. Especially in the case of a substance azeotropically distilled with water or a substance having a strong affinity with water, it is difficult to adequately remove the moisture.

Further, there is a method available in which a solid powder such as molecular sieves or calcium chloride is added to let it adsorb water for dehydration. In this case, it is necessary to remove the solid powder having water adsorbed thereon. As a means for such removal, it is common to employ filtration, but in many cases, it is difficult to remove the solid having water adsorbed thereon.

For example, the moisture in a polyol of a usual grade used as a raw material for the production of urethane, is usually from 1000 to a few hundreds ppm. However, in a case of a grade where the moisture is particularly unwanted, the moisture is required to be not higher than 150 ppm. To remove the moisture in a polyol to a level of from a few hundreds ppm to not higher than 150 ppm, molecular sieves or other solid dehydrating agent, a tetraalkylsilicate or an oligomer obtained by the hydrolysis-dehydration-polycondensation thereof, is used at present. However, in the case of a solid dehydrating agent including molecular sieves, the filtration process is not easy, and in the case of the tetraalkylsilicate or the oligomer obtained by the hydrolysis-dehydration-polycondensation thereof, it takes a long time for dehydration (a few days at room temperature, or about one day at 60° C.).

The present inventors have conducted extensive studies with an aim to develop a useful substance by the reaction of an amino group-containing compound with a silicate and have found that a novel composition obtained by the reaction of a certain specific silicate compound with an amino compound having hydroxyl groups, is an amino compound having a relatively low viscosity and a high boiling point, and such a composition readily reacts with water. The present invention has been accomplished on the basis of this discovery.

DISCLOSURE OF THE INVENTION

The gist of the present invention resides in an amino group-containing silicate composition obtained by reacting a tetraalkoxysilane or a silicate oligomer obtained by hydrolyzing, dehydrating and polycondensing it at a degree of hydrolysis within a range of not higher than 65%, with an amino alcohol having one or two hydroxyl groups, and a dehydrating agent using such a composition.

Now, the present invention will be described in detail. The silicate compound used in the present invention is a tetraalkoxysilane of the following formula or its oligomer:

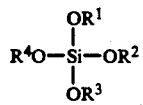

(wherein $R^1$ to $R^4$ which may be the same or different, are a lower alkyl group such as methyl, ethyl, propyl or butyl.)

The silicate oligomer is obtained by hydrolyzing, dehydrating and polycondensing the above tetraalkoxysilane monomer. The production of the oligomer is conducted by adding acidic, neutral or alkaline water in a necessary amount to the tetraalkoxysilane monomer and removing the alcohol resulting from the reaction (which forms 2 molar times the amount of the added water).

The reaction is represented as follows:

$$Si(OR)_4 + nH_2O \rightarrow Si(OR)_{4-2n}O_n + 2nROH \qquad (I)$$

The formula (I) represents the reaction of one molecule of the tetraalkoxysilane. However, in reality, a plurality of molecules are polymerized to form an oligomer.

In the present invention, it is preferred to employ an oligomer having a viscosity of not higher than about 7000 cps (25° C.).

The obtained oligomer is considered to contain not only the one having a chain structure but also condensates having various structures such as branched and cyclic structures and mixtures thereof.

The degree of hydrolysis of the silicate is a value calculated in accordance with the following formula (II), and the amount of water to be added will be determined depending upon the desired degree of hydrolysis.

$$\text{Degree of hydrolysis} = \frac{2n}{4} \times 100 = \frac{n}{2} \times 100 \qquad (II)$$

Namely, in the case where all alkoxy groups of the tetraalkoxysilane have been hydrolyzed, the degree of hydrolysis is 100%, and in the case where two alkoxy groups have been hydrolyzed, the degree of hydrolysis is represented as 50%. The degree of hydrolysis is possible up to 100%. However, the 100% hydrolyzate is complete solid of $SiO_2$. A product wherein the degree of hydrolysis exceeds 70%, is a gel like gelatin, or solid; and a product wherein the degree of hydrolysis is from 65 to 70%, is highly viscous and is likely to react with moisture present in a small amount in air and will be gelled, whereby the storage stability will be poor and handling will be very difficult. Accordingly, in the present invention, it is necessary to use a silicate oligomer having a degree of hydrolysis of up to 65%, and it is preferred to employ an oligomer having a degree of hydrolysis of from 0 to 50%. The tetraalkoxysilane monomer corresponds to a degree of hydrolysis being 0 and will be referred to as an oligomer having a degree of hydrolysis of 0 in this specification.

The amino alcohol used in the present invention is an amino alcohol having at least one primary, secondary or tertiary nitrogen atom and one or two hydroxyl groups, and it may be gas or liquid. Otherwise, it may be solid so long as it is capable of being dissolved in the silicate oligomer or capable of being reacted with the silicate oligomer to form a liquid.

Specifically, it is preferable the one having from 1 to 30 carbon atoms such as methanolamine, ethanolamine, diethanolamine, N-methyldiethanolamine, monomethylethanolamine, dimethylethanolamine, hexanolamine, decyl alcohol amine, pentadecyl alcohol amine, eicosyl alcohol amine or melissyl alcohol amine. However, from the viewpoint of the handling efficiency and the safety, a liquid is preferred, and the one having from 2 to 10 carbon atoms is preferred.

The reaction of the silicate oligomer with the amino alcohol may be conducted by mixing the silicate oligomer and the amino alcohol so that the ratio of the alkoxy equivalent of the silicate oligomer to the hydroxyl equivalent of the amino alcohol becomes a prescribed level and removing from this mixture the alcohol (resulting from the silicate) corresponding to the hydroxyl equivalent. The weight of the silicate oligomer containing one mol of an alkoxy group is one alkoxy equivalent, and when R in the formula (I) is a methyl group, the alkoxy equivalent is represented by the formula (III):

Alkoxy equivalent $$\text{One equivalent} = \frac{28 + 31 \times (4 - 2n) + 16 \times n}{4 - 2n} \quad \text{(III)}$$

When the degree of hydrolysis is 40%, n=0.8, hence, one alkoxy equivalent is 48.

The weight of the amino alcohol containing 1 mol of a hydroxyl group is one hydroxyl equivalent, which is represented by the formula (IV) using the hydroxyl value of the amino alcohol, or the molecular weight and the number of functional groups.

Hydroxyl equivalent $$\text{One equivalent} = \frac{56110}{\text{Hydroxyl value}} = \frac{\text{Molecular weight}}{\text{Number of hydroxyl groups}} \quad \text{(IV)}$$

In the case of ethanolamine, the molecular weight is 61, and the number of hydroxyl groups is 1, hence one hydroxyl equivalent thereof is 61.

The equivalent ratio for the reaction of the silicate oligomer with the amino alcohol is selected within a range of hydroxyl equivalent/alkoxy equivalent=0.1-1.0, preferably 0.4-1.0. The desired equivalent ratio varies depending upon the method of use of the obtained product. In a case where the amino alcohol may remain in excess, the amino alcohol may be used in an excess amount, and likewise in a case where the silicate oligomer may remain, the silicate oligomer may be used in excess. However, the larger the proportion of the amino alcohol, the higher the activity as the dehydrating agent, and when used for the urethane resin, the higher the activity of the reaction for urethane. Accordingly, it is necessary to determine the reaction equivalent ratio depending upon the particular use. If this equivalent ratio is less than 0.1, the effects as a dehydrating agent tend to be very small.

The reaction may be conducted by introducing prescribed amounts of the silicate oligomer and the amino alcohol into a reactor, followed by heating to a temperature of from 70° C. to 200° C., preferably from 100° C. to 160° C., and removing the resulting alcohol. The alcohol and the amino alcohol are likely to lead to azeotropy, and an adequate care is required. This reaction may be conducted in air or in various inert gases, and it may be conducted under atmospheric pressure or reduced pressure. A catalyst may or may not be used. As the catalyst, a usual catalyst for esterification or catalyst for ester exchange may be employed. Specifically, it is possible to employ, for example, an alkyl tin, magnesium acetate, calcium acetate or a titanate.

The resulting product i.e. the amino group-containing silicate composition has high reactivity with water, and an adequate carefulness is required in its handling to avoid the contact with moisture. The viscosity (at 25° C.) of the amino group-containing silicate composition thus obtained is usually from 0.001 to 1000 poise, preferably from 0.01 to 100 poise, more preferably from 0.01 to 10 poise.

The reaction product (the amino group-containing silicate) obtained by the present invention is considered to have constituting units of the following formulas. (1) In a case where the amino alcohol has one hydroxyl group $$Si(OR)_{4-2n-x}O_n(OR')_x \quad \text{(V)}$$

(wherein n is a real number of from 0 to 1.3, $x$ is a real number of from 0.4 to 4, R is an alkyl group, and R' is a monovalent hydrocarbon residue having an amino group.) (2) In a case where the amino alcohol has two hydroxyl groups $$Si(OR)_{4-2n-2y}O_n(OR''O)_y \quad \text{(VI)}$$

(wherein n and R have the same meanings as in the formula (V), $y$ is a real number of from 0.2 to 2, and R" is a bivalent hydrocarbon residue having an amino group.)

The amino group-containing silicate composition of the present invention reacts with water to form an amino alcohol and silicon oxide. By utilizing this reaction, it can be used as a dehydrating agent. The dehydrating agent of the present invention is not suitable for removal of a large amount of water, but is suitable for removing moisture at a level of a few hundreds ppm. By the reaction with water of this level, silicon oxide will not form in such a large extent as it precipitates. Further, particularly when it is used for dehydration of the raw material in the urethane field, the resulting amino alcohol serves as a urethane-forming catalyst, and the amino alcohol will further react with the isocyanate so that it is taken in the resin. And, silicon oxide at a level of a few hundreds ppm will not adversely affect the property of the resin. Especially, this amino groupcontaining silicate composition readily reacts with water, and it takes only a few hours to reduce a moisture of a few hundreds ppm to a level of a few tens ppm.

The composition of the present invention can be used as a dehydrating agent simply by adding the composition of the present invention in a necessary amount to the liquid to be dehydrated, followed by mixing uniformly and leaving the mixture to stand at room temperature for a few hours. To shorten the time for dehydration, the amount of the composition of the present invention may be increased, or the temperature of the liquid to be dehydrated may be raised. Further, the dehydration treatment is preferably conducted in an atmosphere such as nitrogen or dried air which does not contain moisture as far as possible.

The amount of the dehydrating agent composed of the composition of the present invention to be used, is determined depending upon the types of the silicate oligomer and the amino alcohol used as the starting materials and the amount of water in the liquid to be dehydrated.

Namely, the silicate oligomer to be used in the present invention and the structural units of the amino group-containing silicate compositions as the reaction products, are represented by the above formulas (I), (V) and (VI).

And, the amino silicates of the formulas (V) and (VI) can react with (2−n) mol of water, respectively.

Accordingly, if the type of the alkyl group (R) of the raw material silicate compound, the degree of hydrolysis (n/2×100), the type of the amino alcohol (R',R'') and the reaction equivalent ratio of the silicate compound to the amino alcohol (x/(4−2n) or 2y/(4−2n)) are known, the amount of water which can be dehydrated by a prescribed amount of the amino group-containing silicate composition can be calculated.

Practically, the composition of the present invention is added preferably in an amount of from 1 to 5 times, preferably from 1 to 3 times, the calculated amount.

The composition of the present invention may preferably be used particularly for the dehydration of the raw material for the preparation of a urethane resin. The urethane resin is obtained by the dehydration condensation reaction of a polyol with an isocyanate. However, if water is present in the starting material, particularly in the polyol, carbon dioxide gas will be formed by the reaction of water and the isocyanate, thus leading to foaming. As described in the foregoing, the composition of the present invention is capable of removing moisture at a level of a few hundreds ppm as a dehydrating agent, and yet, after the dehydration, it serves as a catalyst for the urethane reaction. Therefore, the dehydrating agent can be used as it is for the reaction for the production of urethane without necessity of removing it.

Likewise, it is particularly useful for dehydration of the raw material for the production of an epoxy resin.

In a case where the amino group-containing silicate composition of the present invention is to be used for a urethane resin, the amino group-containing silicate composition is used as a dehydrating agent for the polyol component. Namely, to the polyol component, a urethaneforming catalyst is added as the case requires, and a necessary amount of the amino group-containing silicate composition is added thereto, and the mixture is left to stand for a few hours. After confirming that the moisture in the polyol mixture is lowered to a level not higher than the objective value (the prescribed value), an isocyanate component is added to this polyol mixture at a equivalent ratio (NCO/OH) of from 1.00 to 1.35, and the mixture is stirred and injected in a mold, followed by curing to prepare a urethane resin.

The polyol component may be those commonly used for the preparation of urethane, including a polyether polyol obtainable by ring-opening addition of an alkylene oxide such as ethylene oxide or propylene oxide using as an initiator water or a hydroxy compound having from 2 to 8 active hydrogen atoms, such as ethylene glycol, propylene glycol, glycerol or trimethylolpropane; a polyester polyol obtainable by reacting a dibasic acid such as adipic acid or phthalic acid with a polyhydric alcohol such as ethylene glycol, propylene glycol or 1,4butanediol; and a polymer polyol obtained by graft polymerizing acrylonitrile and styrene to the abovementioned polyether polyol.

The isocyanate component may be an aliphatic isocyanate such as ethylene diisocyanate, 1,4tetramethylene diisocyanate, 1,6-hexamethylene diisocyanate or 1,12-dodecane diisocyanate; an alicyclic isocyanate such as cyclobutane-1,3-diisocyanate, or cyclohexane-1,3- and -1,4-diisocyanate; an aromatic isocyanate such as m-phenylene diisocyanate, 2,4-tolylene diisocyanate, 2,6-tolylene diisocyanate, or 4,4'-diphenylmethane diisocyanate; or mixtures, oligomers or carbodiimide-modified products thereof.

The urethane-forming catalyst which may be used as the case requires, includes an amine compound such as triethylenediamine, N-methylmorphorine, or tetramethylhexamethylenediamine; and a tin compound such as stannous octoate, stannous oleate, or dibutyltin dilaurate. These catalysts may be used alone or in combination. When such a catalyst is used, it is preferably added in an amount of from 0.01 to 10 parts by weight per 100 parts by weight of the polyol component.

In addition, a crosslinking agent such as ethylene glycol, 1,4-butanediol, or triethanolamine, a pigment such as carbon paste, or a silicone-type foam stabilizer, may be added as the case requires.

Further, the amino group-containing silicate composition of the present invention may be used also as a curing agent at the time of preparing an epoxy resin. Namely, to an epoxy compound having at least one group of the formula

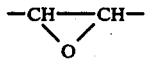

per molecule, the amino group-containing silicate composition of the present invention is reacted in the presence or absence of a catalyst, so that the epoxy equivalent/amine equivalent would be a substantially equal ratio. Specifically, to an epoxy compound as disclosed in e.g. U.S. Pat. Nos. 2,633,458, 2,658,885, 3,373,221 or 3,377,406, the amino groupcontaining silicate composition of the present invention may be added and reacted for curing. Especially, an amino group-containing silicate composition using a silicate oligomer having a low degree of hydrolysis has a low viscosity as compared with conventional epoxy curing agents and a high boiling point as it contains silicon, hence its handling is very easy. The catalyst which may be used for the above reaction includes cationic and anionic catalysts including a tertiary amine (including guanidine, biguanide and imidazole), a boron complex salt, a Lewis acid, an inorganic acid, a short chain amide, dihydrazide and a titanic acid ester. The amount of the catalyst is preferably about a few parts by weight per 100 parts by weight of the epoxy compound. In addition, a diluting agent, a flexibility-imparting agent or a filler, may be added as the case requires.

Figure 1:
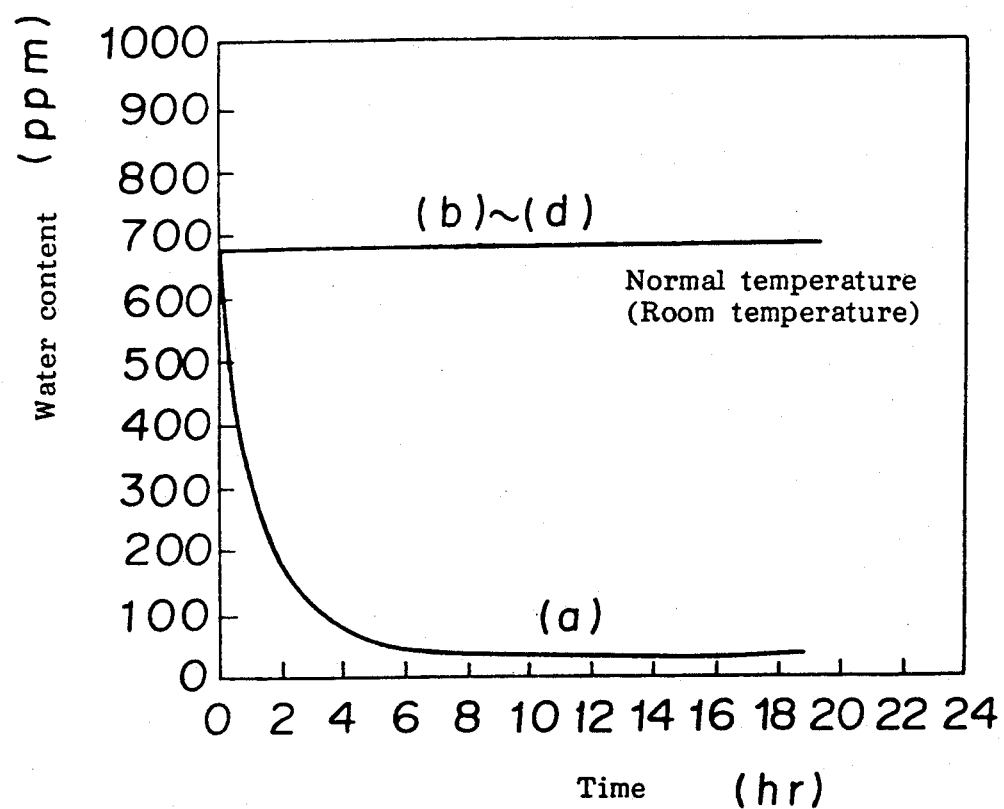
FIG. 1 is a graph showing the changes in the water contents in polyols containing various dehydrating agents prepared in Example 2 of the present invention. In the Figure, (a) to (d) represent the following, respectively.

(a) Polyol/amino group-containing silicate composition of the present invention=100/1.8

(b) Polyol/tetraethylsilicate=100/1.0

(c) Polyol/50% hydrolyzate of tetramethylsilicate=100/0.6

(d) Polyol/tetraethylsilicate/dimethylethanolamine=100/1.0/1.7

EXAMPLES

Now, the present invention will be described in detail with reference to Examples. However, it should be understood that the present invention is by no means restricted to such Examples.

EXAMPLE 1

1 mol of tetraethylsilicate and 4 mols of dimethylethanolamine were introduced into a reactor and heated to 140° C. under a nitrogen atmosphere. The resulting ethanol (about 4 mols) was removed to obtain an amino group-containing silicate composition. The product has a very high reactivity with water, and it is necessary to take a due care in its handling. The viscosity was measured in a nitrogen atmosphere and found to be 0.8 cps (25° C.).

EXAMPLE 2

Dehydration of a polyol was conducted by means of a dehydrating agent (a) composed of the composition of the present invention and other dehydrating agents (b) to (d).

To a polyol mixture (hereinafter referred to simply as "polyol") comprising GP-1000 (a polyol prepared by adding propylene oxide to glycerol, hydroxyl value: 168, manufactured by Sanyo Kasei K. K.) and DPG (dipropylene glycol) at a ratio of 70/30 (weight/weight), (a) the amino group-containing silicate composition obtained in Example 1 was added at a ratio of 100:1.8 (the polyol:the amino group-containing silicate composition, weight/weight), (b) tetraethylsilicate was added at a ratio of 100:1.0 (the polyol:the tetraethylsilicate, weight/weight), (c) a silicate oligomer (hereinafter simply referred to as "oligomer") obtained by hydrolyzing 50% of tetramethylsilicate, was added at a ratio of 100:0.6 (the polyol:the oligomer, weight/weight), and (d) tetraethylsilicate and dimethylethanolamine were added at a ratio of 100:1.0:1.7 (the polyol:the tetraethylsilicate:the dimethylethanolamine, weight/weight/weight), to obtain the respective mixtures, and the changes in the water content with time were measured. The results are shown in FIG. 1.

The conditions were such that the addition and mixing were conducted at room temperature, and the mixtures were left to stand at room temperature, and the water content was measured by a Karl Fischer's method.

The amount of each silicate compound added was an amount capable of dehydrating about 3000 ppm of water.

As is evident from FIG. 1, dehydration was very slow with (b) to (d), whereas dehydration can be conducted in a few hours with (a).

EXAMPLE 3

The mixture (a) in Example 2 (GP-1000/DPG/the amino group-containing silicate composition=70/30/1.8, weight/weight/weight) and polymeric MDI (NCO%: 30.6%, manufactured by MD Kasei K. K.) were reacted at a NCO/OH equivalent ratio of 1.15 in the absence of a catalyst to obtain a non-foamed solid urethane resin.

EXAMPLE 4

To one equivalent of a 50% hydrolyzate of tetramethylsilicate, 0.6 equivalent of monoethanolamine was introduced into a reactor and reacted in the same manner as in Example 1, whereupon the resulting methanol was removed. The obtained amino group-containing silicate composition has a very high reactivity with water in the same manner as in Example 1, and it is necessary to take a due care in its handling. The viscosity in a nitrogen atmosphere at 25° C. was 310 cps. 1.2 Parts by weight of this amino group-containing silicate composition was added to 100 parts by weight of the same "polyol" as used in Example 2, and the water content in the polyol was measured as the time passes. The results are as follows.

| Time passed (hr) | 0 | 2 | 4 | 6 | 10 |
| --- | --- | --- | --- | --- | --- |
| Water content (ppm) | 680 | 180 | 80 | 50 | 30 |

EXAMPLE 5

The amino group-containing silicate composition obtained in Example 4 and Epicote 828 (manufactured by Shell Chemical Co.) were reacted at an epoxy equivalent/amine equivalent=1/1. The obtained resin was equivalent to an epoxy resin cured by a commercially available epoxy resin curing agent (Versamid 125, manufactured by Henkel Hakusuisha K. K.).

INDUSTRIAL APPLICABILITY

The amino group-containing silicate composition of the present invention has a high reactivity with water, is capable of reducing the water content to a very low level and is a low viscosity liquid, whereby its handling is easy and it is useful as a dehydrating agent for various chemical substances.

Further, as it is different from conventional solid dehydrating agents, a process step such as filtration is not required depending upon the field of its application. Further, since it contains a nitrogen atom, it is useful also as a catalyst or a curing agent for a urethane resin or an epoxy resin.

The foregoing characteristics are very effective particularly for the production of a non-foamed urethane resin.

We claim:

1. An amino group-containing silicate composition obtained by reacting a silicate oligomer obtained by hydrolyzing, dehydrating and polycondensing a tetraalkoxysilane at a degree of hydrolysis within a range of from 0 to 65%, with an amino alcohol having one or two hydroxyl groups.

2. The amino group-containing silicate composition according to claim 1, wherein a silicate oligomer obtained by hydrolyzing, dehydrating and polycondensing a tetraalkoxysilane within a range of from 0 to 50%, is used.

3. The amino group-containing silicate composition according to claim 1, wherein the carbon number of the amino alcohol is from 1 to 30.

4. The amino group-containing silicate composition according to claim 1, wherein the carbon number of the amino alcohol is from 2 to 10.

5. A dehydrating agent containing an amino group-containing silicate composition obtained by reacting a silicate oligomer obtained by hydrolyzing, dehydrating and polycondensing a tetraalkoxysilane at a degree of hydrolysis within a range of from 0 to 65%, with an amino alcohol having one or two hydroxyl groups.

6. The dehydrating agent according to claim 5, wherein the amino group-containing silicate composition is the one obtained by reacting the silicate oligomer with the amino alcohol within a range of hydroxyl group equivalent/alkoxy equivalent=0.1–1.0.

7. The dehydrating agent according to claim 6, wherein the hydroxyl group equivalent/alkoxy equivalent is within a range of from 0.4 to 1.0.

8. The dehydrating agent according to claim 5, wherein the silicate oligomer and the amino alcohol are reacted at a temperature of from 70° to 200° C.

9. The dehydrating agent according to claim 5, wherein the viscosity (at 25° C.) of the amino group-containing silicate composition is from 0.001 to 1000 poise.

10. The dehydrating agent according to claim 5, wherein a substance to be dehydrated is a polyol.

11. A non-foamed urethane resin obtained by reacting an isocyanate and a polyol, said polyol or isocyanate, or both said polyol and said isocyanate having a dehydrating agent added thereto, said dehydrating agent being obtained by reacting a silicate oligomer with an amino alcohol having one or two hydroxyl groups, said silicate oligomer obtained by hydrolyzing, dehydrating and polycondensing a tetraalkoxysilane at a degree of hydrolysis within the range of from 0 to 65%.

12. The non-foamed urethane resin according to claim 11, which is obtained by the reaction at a NCO-/OH equivalent ratio of from 1.00 to 1.35.

13. A curing agent for an epoxy resin, which comprises an amino group-containing silicate composition obtained by reacting a silicate oligomer obtained by hydrolyzing, dehydrating and polycondensing a tetraalkoxysilane at a degree of hydrolysis within a range of from 0 to 65%, with an amino alcohol having one or two hydroxyl groups.

14. An amino group-containing silicate composition according to claim 1 wherein said silicate comprises units of the formula:

$$Si(OR)_{4-2n-x}O_n(OR')_x \qquad (V)$$

wherein n is a real number of from 0–1.3, x is a real number of from 0.4 to 4, R is an alkyl group, and R' is a monovalent hydrocarbon residue having an amino group, or comprises units of the formula:

$$Si(OR)_{4-2n-2y}O_n(OR''O)_y \qquad (VI)$$

wherein n and R have the same meaning as in formula V, y is a real number of from 0.2 to 2 and R" is bivalent hydrocarbon residue having an amino group.

15. A dehydrating agent containing an amino group-containing silicate composition according to claim 5 wherein said silicate comprises units of the formula:

$$Si(OR)_{4-2n-x}O_n(OR')_x \qquad (V)$$

wherein n is a real number of from 0–1.3, x is a real number of from 0.4 to 4, R is an alkyl group, and R' is a monovalent hydrocarbon residue having an amino group, or units of the formula:

$$Si(OR)_{4-2n-2y}O_n(OR''O)_y \qquad (VI)$$

wherein n and R have the same meanings as in formula V, y is a real number of from 0.2 to 2 and R" is bivalent hydrocarbon residue having an amino group.

16. A non-foamed urethane resin obtained by reacting an isocyanate and a polyol according to claim 11 wherein the dehydrating agent comprises units of the formula:

$$Si(OR)_{4-2n-x}O_n(OR')_x \qquad (V)$$

wherein n is a real number of from 1–1.3, x is a real number of from 0.4 to 4, R is an alkyl group, and R' is a monovalent hydrocarbon residue having an amino group, or units of the formula:

$$Si(OR)_{4-2n-2y}O_n(OR''O)_y \qquad (VI)$$

wherein n and R have the same meaning as in formula V, y is a real number of from 0.2 to 2 and R" is bivalent hydrocarbon residue having an amino group.

* * * * *

UNITED STATES PATENT AND TRADEMARK OFFICE
CERTIFICATE OF CORRECTION

PATENT NO. : 5,210,246
DATED : May 11, 1993
INVENTOR(S) : Tetsuya Tanaka et al.

It is certified that error appears in the above-indentified patent and that said Letters Patent is hereby corrected as shown below:

On the title page, Item [73],

The second assignee's name is spelled incorrectly, should read:

--Dow Mitsubishi Kasei Limited--

Signed and Sealed this

Twenty-fourth Day of August, 1993

Attest:

BRUCE LEHMAN

*Attesting Officer*     *Commissioner of Patents and Trademarks*